US012620458B2

(12) United States Patent
Eckel et al.

(10) Patent No.: US 12,620,458 B2
(45) Date of Patent: May 5, 2026

(54) METHODS, SYSTEMS, AND COMPUTER READABLE MEDIA FOR AUTOMATED ASSESSMENT OF ASEPTIC TECHNIQUE OF COMPOUNDING IN A COMPOUNDING HOOD

(71) Applicant: The University of North Carolina at Chapel Hill, Chapel Hill, NC (US)

(72) Inventors: Stephen Frederick Eckel, Chapel Hill, NC (US); Robert Charles Hubal, Raleigh, NC (US); Adam Charles Kiefer, Apex, NC (US); Ryan Patrick MacPherson, Chapel Hill, NC (US); Colin Thomas Cabelka, Chapel Hill, NC (US)

(73) Assignee: THE UNIVERSITY OF NORTH CAROLINA AT CHAPEL HILL, Chapel Hill, NC (US)

( * ) Notice: Subject to any disclaimer, the term of this patent is extended or adjusted under 35 U.S.C. 154(b) by 0 days.

(21) Appl. No.: 19/037,106

(22) Filed: Jan. 25, 2025

(65) Prior Publication Data

US 2025/0174309 A1      May 29, 2025

Related U.S. Application Data

(63) Continuation of application No. PCT/US2023/029079, filed on Jul. 31, 2023.
(Continued)

(51) Int. Cl.
 *G16C 20/10*        (2019.01)
 *G16C 20/70*        (2019.01)
(52) U.S. Cl.
 CPC ............. *G16C 20/10* (2019.02); *G16C 20/70* (2019.02)

(58) Field of Classification Search
 None
 See application file for complete search history.

(56) References Cited

U.S. PATENT DOCUMENTS

2011/0191121 A1    8/2011  Fioravanti
2016/0200462 A1    7/2016  Kriheli et al.
(Continued)

FOREIGN PATENT DOCUMENTS

JP        2017-109822 A      6/2017
JP        2021-109749 A      8/2021
(Continued)

OTHER PUBLICATIONS

Regmi, Hem, Jerry Nesamony, and Vijay Devabhaktuni. "A new computational decision support system for material selection and real-time monitoring and evaluation of aseptic technique when compounding sterile preparations." Journal of Pharmaceutical Innovation 12.2 (2017): 124-141. (Year: 2017).*
(Continued)

*Primary Examiner* — Karlheinz R. Skowronek
*Assistant Examiner* — Mary C Leverett
(74) *Attorney, Agent, or Firm* — Jenkins, Taylor & Hunt, P.A.

(57)        ABSTRACT

A method for automated assessment of aseptic technique of compounding in a compounding hood includes collecting, using sensors positioned in or around a compounding hood, data from which positions, orientations, and movements of objects used in an aseptic compounding task can be determined. The method further includes feeding the data into an automated aseptic technique evaluator. The method further includes identifying, using the automated aseptic technique evaluator and from the data, phases of the aseptic compounding task. The method further includes automatically detecting, by the automated aseptic technique evaluator,
(Continued)

errors occurring during at least some of the phases. The method further includes generating and displaying, by the automated aseptic technique evaluator, output indicative of the errors.

22 Claims, 7 Drawing Sheets

Related U.S. Application Data

(60) Provisional application No. 63/393,766, filed on Jul. 29, 2022.

(56) References Cited

U.S. PATENT DOCUMENTS

| | | |
|---|---|---|
| 2020/0043604 A1 | 2/2020 | Singh et al. |
| 2022/0139089 A1 | 5/2022 | LeFranc et al. |

FOREIGN PATENT DOCUMENTS

| | | |
|---|---|---|
| KR | 10-2022-0086593 A | 6/2022 |
| WO | WO 2017/072854 A | 5/2017 |
| WO | WO 2022/072358 A | 4/2022 |

OTHER PUBLICATIONS

Regmi, Hem Kanta. A real-time computational decision support system for compounded sterile preparations using image processing and artificial neural networks. MS thesis. University of Toledo, 2016. (Year: 2016).*

Vasandani, Juily, et al. "Improving Model Accuracy with Probability Scoring Machine Learning Models." Advances in Data Science and Information Engineering: Proceedings from ICDATA 2020 and IKE 2020. Cham: Springer International Publishing, 2021. 517-530. (Year: 2021).*

Lebel, Denis, Maxime Thibault, and Jean-François Bussières. "Asynchronous validation and documentation of sterile compounding in a hospital pharmacy." The Canadian Journal of Hospital Pharmacy 63.4 (2010): 323. (Year: 2010).*

Farcy, Elisabeth, et al. "Use and impact of technology-assisted workflow (TAWF) systems for drug compounding in pharmacy practice: a scoping literature review." Pharmaceutical Technology in Hospital Pharmacy 6.1 (2021): 20210009. (Year: 2021).*

Notification of Transmittal of the International Search Report and the Written Opinion of the International Searching Authority, or the Declaration for International Patent Application Serial No. PCT/US2023/029079 (Nov. 9, 2023).

Instruction on compounded sterile preparations at schools of pharmacy. American Journal of Health-System Pharmacy 2018;75(12):847-849.

Accreditation Council for Pharmacy Education: PharmD Program Accreditation. ACPE Standard 2016 https://www.acpe-accredit.org/pdf/Standards2016FINAL.pdf (last accessed Mar. 1, 2019).

Moody CA, Eckel SF, and Amerine LB. Evaluating the sensitivity of a media-fill challenge test under various situations as a reliable method for recommended aseptic technique competency assessment. Journal of Pharmacy Technology 2016;32(2):47-53.

Kastango ES. A practical guide to aseptic technique verification: policies and procedures that meet USP Chapter 797 requirements. Pharmacy Purchasing and Products Apr. 2005: 16-18 https://www.pppmag.com/documents/V2N2/Aseptic.pdf (last accessed Mar. 1, 2019).

Lee RK and Shrewsbury RP, Potency Analyses Provide Insight Into Student Aseptic Compounding Technique Errors. American Journal of Pharmaceutical Education 2019; 83(9), Article 7338.

Triad Rx, Inc US Food & Drug Administration Form 483 Warning letter: Feb. 5, 2019: https://www.fda.gov/ICECI/EnforcementActions/WarningLetters/ucm631101.htm (last accessed Mar. 1, 2019).

Newton DW and Trissel LA. A primer on USP Chapter 797: "Pharmaceutical compounding sterile preparations," and USP Process for Drug and Practice Standards. International Journal of Pharmaceutical Compounding 2004;8(4):251-263.

Myers CE. History of sterile compounding in US hospital: Learning from the tragic lessons of the past. American Journal of Health-System Pharmacy 2013;70:1414-1427.

Newton DW. United States Pharmacopela Chapter <797> Timeline: 1989 to 2013. International Journal of Pharmaceutical Compounding 2013;17(4): 283-288.

Morris AM, Schneider PJ, Pedersen CA, and Mirtallo JM. National survey of quality assurance activities for pharmacy-compounded sterile preparations. American Journal of Health-System Pharmacy 2003;60:2567-2576.

Vonberg RP and Gastmeier P. Hospital-acquired infections related to contaminated substances. Journal of Hospital Infection 2007;65:15-23.

Woodcock J and Dohm J. Toward Better-Quality Compounded Drugs—an Update from the FDA. New England Journal of Medicine 2017;377(26):2509-2512.

Shehab N, Brown MN, Kallen AJ, and Perz Jf. US Compounding Pharmacy-Related Outbreaks, 2001-2013: Public Health and Patient Safety Lessons Learned. Journal of Patient Safety 2018;14(3):164-173.

Statement of Janet Woodcock, M.D. before the subcommittee on health of the committee on energy and commerce—'Reforming the drug compounding regulatory framework; Jul. 16, 2013: http://docs.house.gov/meetings/IF/IF14/20130716/101137/HHRG-113-IF14-Wstate-WoodcockJ-20130716-U1.pdf.

New England Compounding Center meningitis outbreak: https://en.wikipedia.org/wiki/New_England_Compounding_Center_meningitis_outbreak (last accessed Mar. 1, 2019).

Office Action for Japanese Patent Application Serial No. 2025504825 (Jan. 13, 2026).

Office Action for Canadian Patent Application Serial No. 3263056 (Mar. 5, 2026).

* cited by examiner

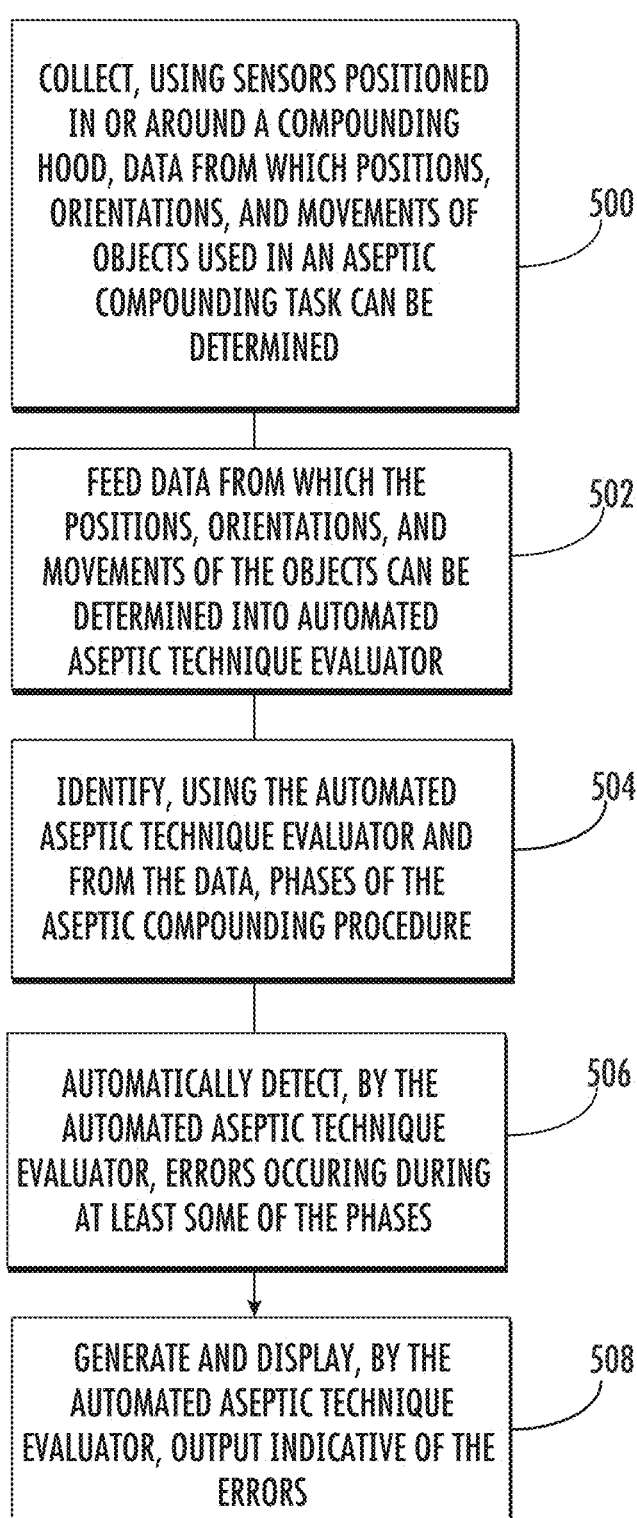

COLLECT, USING SENSORS POSITIONED IN OR AROUND A COMPOUNDING HOOD, DATA FROM WHICH POSITIONS, ORIENTATIONS, AND MOVEMENTS OF OBJECTS USED IN AN ASEPTIC COMPOUNDING TASK CAN BE DETERMINED — 500

FEED DATA FROM WHICH THE POSITIONS, ORIENTATIONS, AND MOVEMENTS OF THE OBJECTS CAN BE DETERMINED INTO AUTOMATED ASEPTIC TECHNIQUE EVALUATOR — 502

IDENTIFY, USING THE AUTOMATED ASEPTIC TECHNIQUE EVALUATOR AND FROM THE DATA, PHASES OF THE ASEPTIC COMPOUNDING PROCEDURE — 504

AUTOMATICALLY DETECT, BY THE AUTOMATED ASEPTIC TECHNIQUE EVALUATOR, ERRORS OCCURING DURING AT LEAST SOME OF THE PHASES — 506

GENERATE AND DISPLAY, BY THE AUTOMATED ASEPTIC TECHNIQUE EVALUATOR, OUTPUT INDICATIVE OF THE ERRORS — 508

METHODS, SYSTEMS, AND COMPUTER READABLE MEDIA FOR AUTOMATED ASSESSMENT OF ASEPTIC TECHNIQUE OF COMPOUNDING IN A COMPOUNDING HOOD

PRIORITY CLAIM

This application is a continuation of PCT Patent Application No. PCT/US2023/029079, filed Jul. 31, 2023, which claims the priority benefit of U.S. Provisional Patent Application Ser. No. 63/393,766, filed Jul. 29, 2022, the disclosure of each of which is incorporated herein by reference in its entirety.

TECHNICAL FIELD

The subject matter described herein relates to tracking aseptic technique during compounding in a compounding hood, defined as a biological safety cabinet, a laminar airflow workbench, or other similar device. More particularly, the subject matter described herein relates to automated tracking and characterizing of aseptic technique of compounding in a compounding hood.

BACKGROUND

In 2012, a tragedy occurred in sterile compounding that garnered national attention. The New England Compounding Center (NECC) had compounded sterile methylprednisolone injections that were distributed to 23 different states. Unfortunately, these were contaminated with a fungus that led to meningitis in patients receiving the compounded product, resulting in over 800 individuals being sickened and 76 deaths.[1] Besides this alarming event, many other compounding tragedies have occurred but not received the same attention.[2-9]

Since the NECC meningitis outbreak in 2012, the FDA has increased its oversight of compounding pharmacies. Before that event, these businesses were monitored by state boards of pharmacy and were infrequently inspected against United States Pharmacopeia guidance documents. In 2013, the Drug Quality and Security Act was passed and gave more authority to the FDA to oversee compounding. This amended the Federal Food, Drug, and Cosmetic Act to create two categories of compounded products based upon risk level for the patient: compounding pharmacies (section 503a) and outsourcing facilities (section 503b). Since this became law, understanding the various regulations, preparing the pharmacy for compliance, and educating employees on appropriate aseptic technique has been a major focus for all employers. This includes both hospitals and community pharmacies.

Despite this increased attention, however, there continues to be issues with compounded products as documented by the FDA through inspections. A warning letter (Form FDA 483) posted on Feb. 5, 2019 to a compounding pharmacy indicated that FDA inspectors found serious deficiencies in preparing sterile drug products. Some of the violations that were noted from this inspection include:[10]

Personnel were observed conducting aseptic manipulations that blocked the movement of first pass air over and around open vials.
  The media fills were not performed under the most challenging or stressful conditions.
  Personnel engaged in aseptic processing were observed with exposed hands and wrists in the ISO 5 area.

The inspectors noted a "lack of assurance" in aseptically producing drug products within the facility.

To prevent the compounding of a contaminated product, one needs to have appropriate facilities, policies and procedures—and, importantly, the ability to train, assess, and maintain competency for employees on aseptic technique. Facilities and policies are readily assessed, but procedures to ensure that pharmacists and technicians—every employee—always follow strict aseptic technique on every preparation is difficult. The usual method for training, assessing, and maintaining competency is for the employee to be observed while making various preparations. Over time, the employee gets signed off as competent and is then allowed to prepare compounded sterile products with little to no oversight. Observation has been demonstrated to be a poor technique for assuring accuracy in compounding.[11] Each employee must also complete annual media fill tests, simulating different compounded preparations.[12] These tests require making different products using tryptic soy broth as a medium; if the employee demonstrates poor technique, the medium becomes contaminated. While the concept seems to be sound, research demonstrates that it is difficult to seed a positive. This research involved evaluating media fill tests of sensitivity and specificity when using poor technique.[13] A total of 250 simulated compounded preparations were prepared. The first manipulation (25 preparations) followed best-practice aseptic technique and sterile compounding procedures. Each of the following 4 sets of manipulations removed one aspect of best-practice aseptic technique to the point whereby the preparation was made without any alcohol to sterilize the vial septum, the preparer used no gloves, the preparation was made outside of the compounding hood, and the uncapped vial was left 24 hours in 'dirty' air before preparation. Even though such poor conditions were utilized, no single preparation showed signs of turbidity, sedimentation, or visible microbial growth. A 0% contamination rate was documented. If the only option for ensuring that an employee is competent is through observation and media fill tests, which both have been demonstrated to be poor markers for proper compounding processes, then the false impression that an employee is competent exists and the potential for a wrong product to reach the patient is high.[11,13]

There is also a requirement that all pharmacy students be trained on aseptic technique, not only employees at compounding pharmacies. The Accreditation Council for Pharmacy Education (ACPE) Standards 2016 states that all pharmacy schools must provide aseptic didactic training: 'Preparation of sterile and non-sterile prescriptions which are pharmaceutically accurate regarding drug product and dose, free from contamination, and appropriately formulated for safe and effective patient use'.[14] The method used, and the time focused on this important skill is varied. A recent survey found 'only 59% of schools believed that their students were adequately trained in compounding sterile preparations'.[15]

In light of these and other difficulties, there exists a need for improved methods, systems, and computer readable media for automated assessment of aseptic technique of compounding in a compounding hood.

SUMMARY

A method for automated assessment of aseptic technique of compounding in a compounding hood includes collecting, using sensors positioned in or around a compounding hood, data from which positions, orientations, and movements of objects used in an aseptic compounding task can be determined. The method further includes feeding the data into an automated aseptic technique evaluator. The method further includes identifying, using the automated aseptic technique evaluator and from the data, phases of the aseptic compounding task. The method further includes automatically detecting, by the automated aseptic technique evaluator, errors occurring during at least some of the phases. The method further includes generating and displaying, by the automated aseptic technique evaluator, output indicative of the errors.

According to an aspect of the subject matter described herein, collecting the data using the sensors positioned in or around the compounding hood includes collecting the data using cameras or other sensors positioned in or around the compounding hood. Examples of other types of sensors that may be used include heat, infrared, and acoustic sensors.

According to another aspect of the subject matter described herein, collecting the data using the sensors positioned in or around the compounding hood includes collecting the data using Internet of Things (IoT) sensors located on compounding instruments or compounding materials.

According to another aspect of the subject matter described herein, identifying the phases includes applying a computer-vision-based object detection model to identify the objects.

According to another aspect of the subject matter described herein, identifying the phases includes using a computer-vision-based pose estimation model to create time series data representing positions, orientations, and movements of the objects at different times.

According to another aspect of the subject matter described herein, identifying the phases includes utilizing task phase identification heuristics to identifying each phase.

According to another aspect of the subject matter described herein, automatically detecting the errors includes applying a classification model that generates, for each phase, a probability score—based on the time series data and expected positions, orientations, and movements of the objects—indicative of a likelihood of occurrence of an error and determining that the error has occurred when the score exceeds a threshold value, differentiating actual and expected positions, orientations, and movements of the objects.

According to another aspect of the subject matter described herein, generating and displaying the output includes generating and displaying a dashboard interface that indicates the errors that occurred during performance of the aseptic compounding task.

According to another aspect of the subject matter described herein, the dashboard interface displays in real time during performance of the aseptic compounding task best practice advisory actions for a student/user to perform during the aseptic compounding task.

According to another aspect of the subject matter described herein, the automated aseptic technique evaluator is implemented using at least one trained machine learning classifier.

According to another aspect of the subject matter described herein, a system for automated assessment of aseptic technique of compounding in a compounding hood is provided. The system includes at least one processor. The system further includes a plurality of sensors positionable in or around a compounding hood for collecting data from which positions, orientations, and movements of objects used in an aseptic compounding task can be determined. The system further includes an automated aseptic technique evaluator implemented using the at least one processor for receiving the data, identifying from the data phases of the aseptic compounding task, automatically detecting errors occurring during at least some of the phases, and generating and displaying output indicative of the errors.

According to another aspect of the subject matter described herein, the sensors comprise cameras or other optical sensors positionable in or around the compounding hood.

According to another aspect of the subject matter described herein, the sensors comprise Internet of Things (IoT) sensors locatable on compounding instruments or compounding materials.

According to another aspect of the subject matter described herein, the automated aseptic technique evaluator is configured to use a computer-vision-based object detection model to identify the objects.

According to another aspect of the subject matter described herein, the automated aseptic technique evaluator is configured to use a computer-vision-based pose estimation model to create time series data representing positions and orientations of the objects at different times.

According to another aspect of the subject matter described herein, the automated aseptic technique evaluator is configured to utilize task phase identification heuristics to identify each phase.

According to another aspect of the subject matter described herein, the automated aseptic technique evaluator is configured to detect the errors by applying a classification model that generates, for each phase, a probability score indicative of a likelihood of occurrence of an error and determining that the error has occurred when the score exceeds a threshold value.

According to another aspect of the subject matter described the automated aseptic technique evaluator is configured to generate a dashboard interface that indicates the errors that occurred during the performance of the aseptic compounding task.

According to another aspect of the subject matter described herein, the automated aseptic technique evaluator is implemented using at least one trained machine learning classifier.

According to another aspect of the subject matter described herein, a non-transitory computer readable medium having stored thereon executable instructions that when executed by the processor of a computer control the computer to perform steps is provided. The steps include collecting, using sensors positioned in or around a compounding hood, data from which positions, orientations, and movements of objects used in an aseptic compounding task can be determined. The steps further include feeding the data into an automated aseptic technique evaluator. The steps further include identifying, using the automated aseptic technique evaluator and from the data, phases of the aseptic compounding task. The steps further include automatically detecting, by the automated aseptic technique evaluator, errors occurring during at least some of the phases. The steps further include generating and displaying, by the automated aseptic technique evaluator, output indicative of the errors.

The subject matter described herein can be implemented in software in combination with hardware and/or firmware. For example, the subject matter described herein can be implemented in software executed by a processor. In one exemplary implementation, the subject matter described herein can be implemented using a non-transitory computer readable medium having stored thereon computer executable instructions that when executed by the processor of a computer control, the computer, to perform steps. Exemplary computer readable media suitable for implementing the subject matter described herein include non-transitory computer-readable media, such as disk memory devices, chip memory devices, programmable logic devices, and application specific integrated circuits. In addition, a computer readable medium that implements the subject matter described herein may be located on a single device or computing platform or may be distributed across multiple devices or computing platforms.

BRIEF DESCRIPTION OF THE DRAWINGS

Exemplary implementations of the subject matter described herein will now be explained with reference to the accompanying drawings, of which:

FIG. 5 is a flow chart illustrating an exemplary process for automated assessment of aseptic technique;—

DETAILED DESCRIPTION

Figure 1:
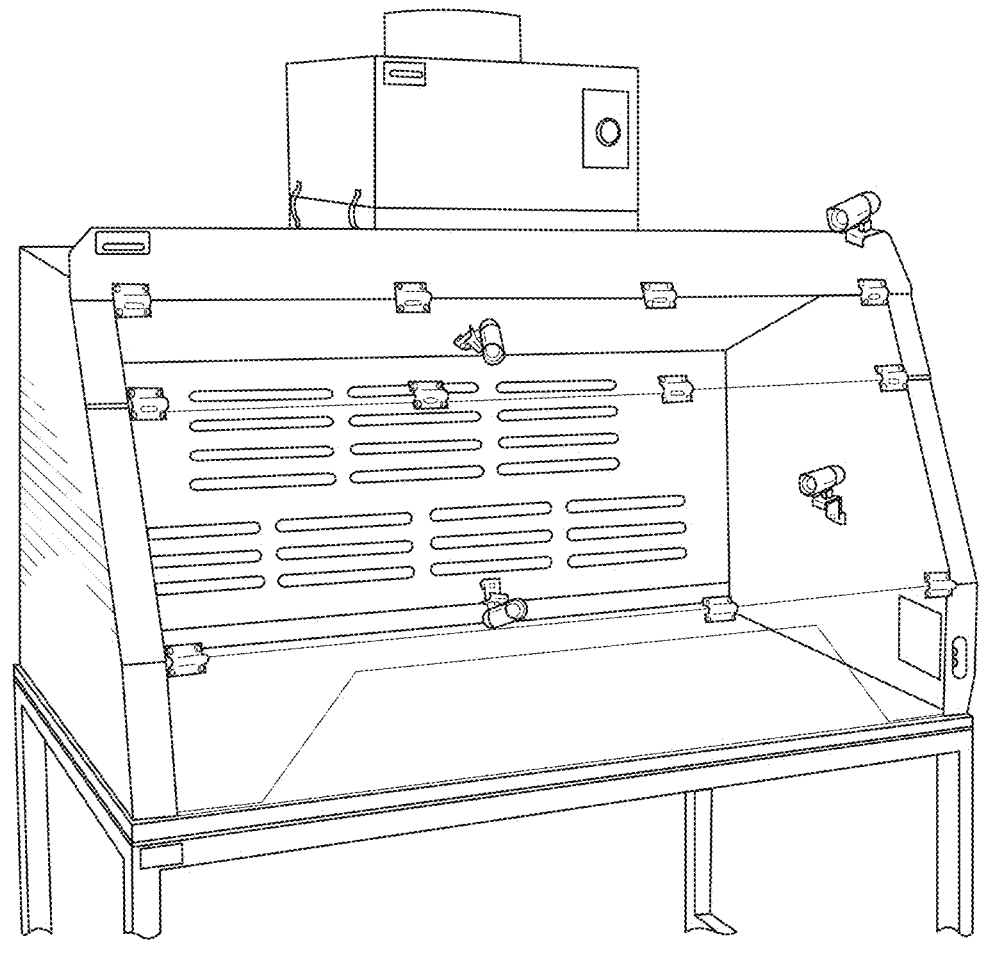
FIG. 1 is an exemplary image of a compounding hood including cameras positioned at different locations in the cabinet for capturing video of a student/user performing a compounding task.

Because of the need described above, the subject matter described herein includes automated assessment of aseptic technique of compounding in a compounding hood. In one exemplary implementation, aseptic technique is evaluated by capturing, using cameras or other optical sensors positioned in or around a compounding hood, video images of a student/user performing a pharmaceutical compounding task. The video images are processed to identify aseptic equipment, movement of the equipment, and actions of the student/user during compounding. An automated aseptic technique evaluator implemented in software evaluates the movements and actions using aseptic technique evaluation rules, examples of which will be described below. The automated aseptic technique evaluator includes a dashboard interface that displays evaluation results to the student/user.

In one study, equipment used during aseptic technique was tracked using chips containing accelerometers and gyroscopes located on aseptic equipment (e.g., syringes, vials) to record movement. When doing this, it was determined that tolerances for aseptic technique had not been developed. Even though there is an expectation for student/users to follow principles of aseptic technique, these steps are generalities and have been formed by opinions over decades as opposed to a robust body of literature testing each step to determine performance indicators on what is appropriate and what is not. To overcome this issue, experts in the field were convened for focus groups to determine specific tolerances for each step. Utilizing a modified Delphi approach, specific tolerances that guide each step of the process when compounding in a compounding hood were identified. This is the first time that quantitative standards have been defined and is a component of the engine which drives the automated aseptic technique evaluator as one is able to determine compliance.

The automated aseptic technique evaluator may assess individuals when compounding sterile products during normal workflow, by documenting movements and comparing movements against established best practice as identified through tolerances above. Following completion of each product preparation, individuals may receive defensible performance reports, including any breaches of technique and steps to resolve for future preparations. This documentation can be used for training of new individuals, assessing ongoing competency of current employees, or providing documentation to regulators (state boards of pharmacy; hospital accrediting bodies; FDA) on ongoing quality assurance with aseptic technique. This real-time feedback will also guide the pharmacist on whether the product should be re-made because a breach of aseptic technique occurred and not be administered to the patient.

The need for aseptic technique quantification and evaluation centers around the concept that there will continue to be increasing regulatory and financial pressure focused on the compounding of intravenous (IV) medications. Hospitals, compounding community pharmacies, and compounding manufacturers not only have to ensure the accuracy and precision of the final preparation, but also need to focus on the environment in which the product was made, the steps the individual followed during compounding, and maintaining the documentation to satisfy accreditation and regulatory agencies. One of the most important activities is aseptic technique, the steps used by the individual in preparing the product. If there are any breaches in this process, the final product could be contaminated.

In one example, the automated aseptic technique evaluator may be implemented using an artificial intelligence (AI) engine that is trained to determine whether captured video portrays aseptic technique evaluation rules that are followed or not and to generate output that quantifies the degree to which aseptic technique was followed. The output can be used for training, quality assurance, or other purposes. In one example, data collection and evaluation may include wireless transmission of captured video from the cameras to a server, kinematic data pipeline automation to assess the captured video using an AI tool, and storage of data such that it can be readily accessed. The system may yield a time series analysis of the videos by computing specified biomechanical variables (e.g., joint angle in x, y, z and pitch, yaw, roll) at each time step.

In one exemplary implementation, commercial off-the-shelf USB cameras may be placed within a standard compounding hood and used to capture movement during aseptic technique. One type of compounding hood that may be used is a horizontal airflow IV hood. Another type is a vertical airflow IV hood. The cameras may be located at various locations in the compounding hood, for example, for the horizontal airflow IV hood, at the locations illustrated in FIG. 1. For each combination of three cameras, an origin for the motion capture system may be determined. The cameras may be used to capture video for pharmaceutical compound preparations, and the video may be output in a computer-readable format, such as mpeg (.mp4) format. The subject matter described herein is not limited to using three cameras. For example, more or fewer than three cameras may be used without departing from the scope of the subject matter described herein. For another example, sensing methods alternative to optical may be used without departing from the scope of the subject matter described herein.

Once the images are captured, machine learning may be applied to the captured data. Specific movements and actions may be marked such that the algorithm will know to distinguish between better and worse performance. The training itself may take place in cycles; in one exemplary implementation, as each batch of 25-30 videos is captured, the videos may be fed to the machine learning model for continuous refinement. After each refinement, the models may be integrated into a motion capture system-based library to extract data and create a generalizable database structure for visualizing the assessment of performance.

Figure 2:
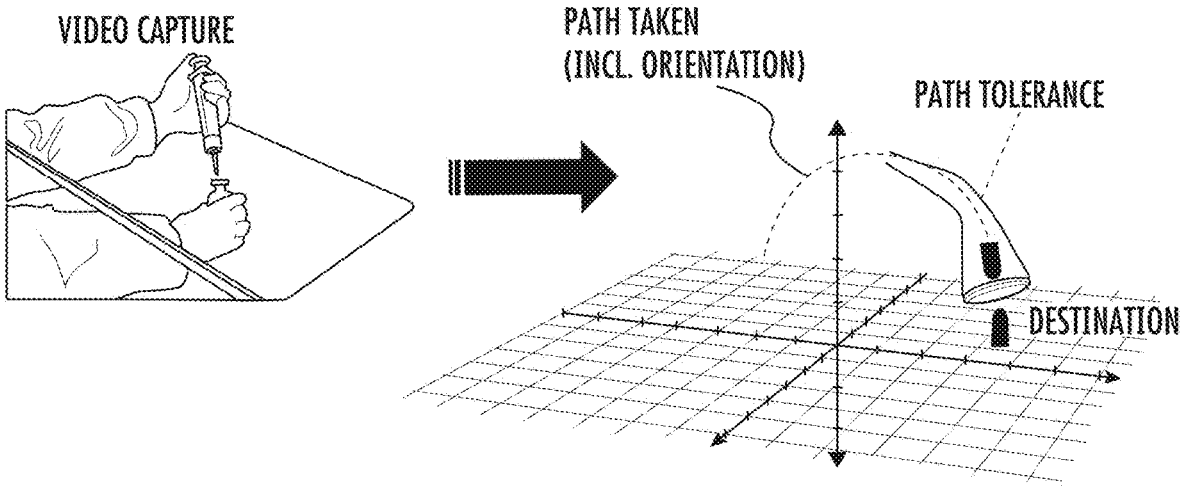
FIG. 2 is a schematic diagram illustrating the exemplary tracking of motion of a student/user and equipment during a pharmaceutical compounding task and the mapping of the motion into a 3D coordinate system including a path tolerance for movements of tracked objects.

The automated aseptic technique evaluator may include a template for presentation of data. The template may be reusable across use cases (e.g., assessing non-sterile compounding technique or compounding of topical or oral solutions (non-IV) as well as aseptic (IV) technique) but specific data visualization elements may need to be specified to adequately mine the machine learned results and display the results clearly on a dashboard. In one example, movement data output from and post-processed by the motion capture system may be linked to show activity via a dynamic html reporting system. For example, it may be specified how to extract movement associated with blocking airflow by poor positioning of an item versus actions such as poor technique in extracting liquids or cleaning exposed surfaces. Measures may be tracked during the aseptic practice (the arc of movement, its staying within or exceeding bounds, and its correctness depending on the given aseptic task; see FIG. 2). The motion capture system may have the potential for specific parameters of playback that will inform visualization (e.g., regions of interest, 3D model display of human mover, etc.). The intent here is to visualize activity and tolerance boundaries, which may be refined through expert reviews. Data from the motion capture system may be mapped to a coordinate system and displayed along with path tolerances for movement of aseptic equipment (see FIG. 2).

The automated aseptic technique evaluator may display data in a dashboard form (listing out all the steps and evaluation of how the compounder performed against them) as well as a customized report. This report may track how a compounder has performed over time (e.g., as a student/user license) or can be used to compile all compounders in a certain work setting (institutional license). This information may be used for ongoing competency assessment to provide to instructors or regulators.

The solution described herein can address both education and training of individuals on aseptic technique as well as quality assurance and compliance. The automated aseptic technique evaluator, in one example, may be implemented as a stand-alone product available via a software license. In another example, the automated aseptic technique evaluator may be integrated with a compounding hood or compounding hood that also includes cameras or other sensors to track motion.

The automated aseptic technique evaluator may be used to evaluate aseptic technique in horizontal and vertical compounding hoods. The automated aseptic technique evaluator may be continually refined using machine learning. Machine learning may include identifying an unsupervised learning mechanism to feed data and training the mechanism using a learning set (75-80%) of captured .mp4 files and rubric ratings from independent raters; testing the learning using a testing set (20-25%) of captured .mp4 files and comparing outputs to rubric ratings. It is stressed that this is a different type of machine learning that is presented above. Here, the goal is to learn patterns in movement that indicate better or worse performance that ultimately do not need to be annotated, and that may differ from expert-defined patterns. This testing also includes having the mechanism automatically determine tolerances accounting for differences in the practice of aseptic technique, from as overt as horizontal vs. vertical airflow to more subtle features such as characteristics of the compounder. This testing may also involve determining the feasibility of different camera setups, as exemplified by the placement for settings where three cameras are viable vs. those where only two are viable.

Additional features of the automated aseptic technique evaluator may include a dashboard for instructor selection of activity and associated tolerances, automated blurring of identifying detail (e.g., faces), real time or near real-time capture and evaluation of aseptic activity, and incorporation of IoT sensors on devices, the compounding hood, or the student/user.

Figure 3:
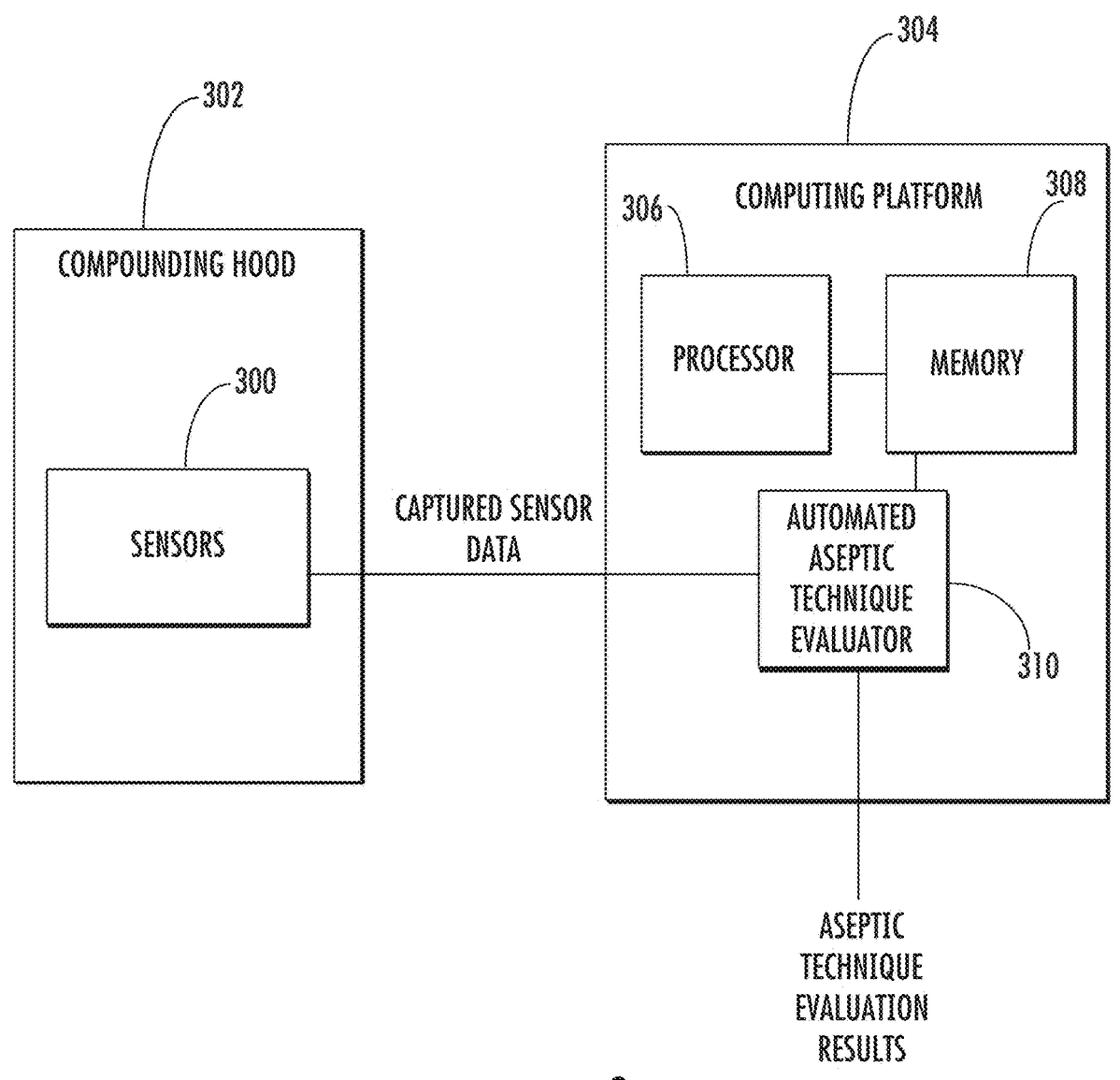
FIG. 3 is a block diagram of an exemplary system for automated assessment of aseptic technique.

FIG. 3 is a block diagram illustrating an exemplary system for automated evaluation of aseptic technique. Referring to FIG. 3, the system includes one or more sensors 300 located in or around a compounding hood 302. The system further includes a computing platform 304 including at least one processor 306 and a memory 308. The system further includes an automated aseptic technique evaluator 310, which may be implemented using computer executable instructions stored in memory 308 and executed by processor 306. Sensors 300 may include any suitable sensors for capturing images and movements of aseptic equipment, compounds, and the students/users in or around compounding hood 302. In one example, sensors 300 may include optical sensors, such as cameras. In another example, sensors 300 may include IoT devices that are integrated in or on aseptic equipment, such as syringes, vials, etc. Sensors 300 produce output data which is fed into an automated aseptic technique evaluator 310. Automated aseptic technique evaluator 310 evaluates the aseptic technique using one or more trained machine learning algorithms and generates output indicative of the quality of performance of aseptic technique. In one example, automated aseptic technique evaluator 310 may be implemented using a multi-stage machine learning classifier that performs the following operations:

1) Applies a computer vision (CV)-based object detection model to each perspective video, creating 2D or 3D positional time series data for task-relevant objects in a scene.

2) Applies a CV-based pose estimation model to each perspective video, creating time series data representing the position and orientation of the relevant human behaviors in the scene.

3) Utilizes the object detection and pose estimation data to demarcate (e.g., timestamp) phases of the task performance utilizing a ruleset comprised of aseptic technique task phase identification heuristics.

4) For each identified task phase, applies a classification model that generates probability scores representing the likelihood that any task errors from an a priori list occurred during the phase.

5) Records and/or presents to the student/user any errors for which the probability score exceeds a set threshold (e.g., the error most likely occurred)

For step 1, an example of the computer vision model is an AI model that is trained to recognize objects that will be present in a compounding hood during aseptic technique. Examples of such objects are the student's/user's hands, vials, syringes, compounds, cleaning materials, etc. Positional time series data includes timestamped locations of the objects in the coordinate system defined for each camera or other sensor. An algorithm for tracking position, orientation, and movement of the gloved hands of the user will be described below.

For step 2, the pose estimation model estimates pose and orientation of objects captured by the sensors. For example, the pose estimation model may estimate the orientation and position of a vial as the student/user moves the vial during a compounding task.

For step 3, timestamp data is added to the pose estimation data from step 2 for each identified object. The result of adding the timestamp data to the pose estimation data is a quantification of movement of an identified object in the scene. For example, the object may be a syringe, and the tracked movement may be the injection of the needle connected to the syringe in the vial, the movement of the plunger to withdraw the liquid from a vial, and then the removal of the syringe with the needle intact from the vial. This process must ensure that the syringe with intact needle is facing the first air, the student's/user's hands are not blocking the first air going toward the syringe with intact needle or vial, and each step is conducted in a manner to ensure the sterility of the compounded product. An example of an aseptic technique task phase identification heuristic is a heuristic that identifies a compound withdrawal event.

For step 4, an example of rules that may be used to determine whether or not an error occurred will now be described. The example relates to compounding using a compounding hood and involves the following steps:

Assembling the syringe and needle

The goal is to prevent contamination originating from materials entering the compounding hood and ensure only clean air is present around critical sites when assembling syringe Sources of error include Attaching needle to syringe away from the HEPA filter (blocks sterile air at needle attachment point)

Failing to wipe down packaging or the exterior of all syringes, needles, IV bags, and materials entering compounding hood with 70% isopropyl solution or pre-soaked alcohol wipes.

Placing an object or a hand so as to block airflow to syringe

Unwrapping the syringe by opening the package toward the compounder rather than the HEPA filter Withdrawing liquid from a vial The goals are to ensure that injection sites are sterilized, inject sterile air into the vial to match volume withdrawn, and keep all transfer sites in clean air.

Sources of error include

Facing the bevel of the syringe toward the compounder

Failing to disinfect with alcohol

Inserting the needle outside of 10-110° range (may contribute to coring)

Leaving the vial with positive or negative pressure.

Not changing the needle after each insertion.

Placing an object or a hand so as to block airflow to the injection site.

Placing an object or a hand so as to block airflow to the uncapped vial.

Placing an object or hand so as to block airflow to the vial's rubber stopper

Scrubbing the vial stopper back and forth (may introduce particulates)

Uncapping needle toward compounder, blocking airflow to the needle.

Withdrawing an incorrect amount of air into the syringe

Withdrawing liquid but having bubbles present

Injecting into an IV bag

The goal is to safely remove air from the needle, inject medication into an IV bag with clean air, and safely dispose of sharps Sources of error include Having uncapped syringe not facing the HEPA filter at any time Failing to wipe down an IV bag or injection port.

Placing object or hand so as to block airflow to injection site airflow

Using a needle to pierce outside intended injection path

Additional areas of focus:

Performs all operations at least 6" inside and 3" from the back of the compounding hood Arranges items in the compounding hood such that nothing comes between the HEPA filter and sterile items, and avoids extraneous items in the compounding hood Disposes of materials appropriately (needles in sharps container; syringe, paper, alcohol wipes, etc., in trash container)

Figure 4:
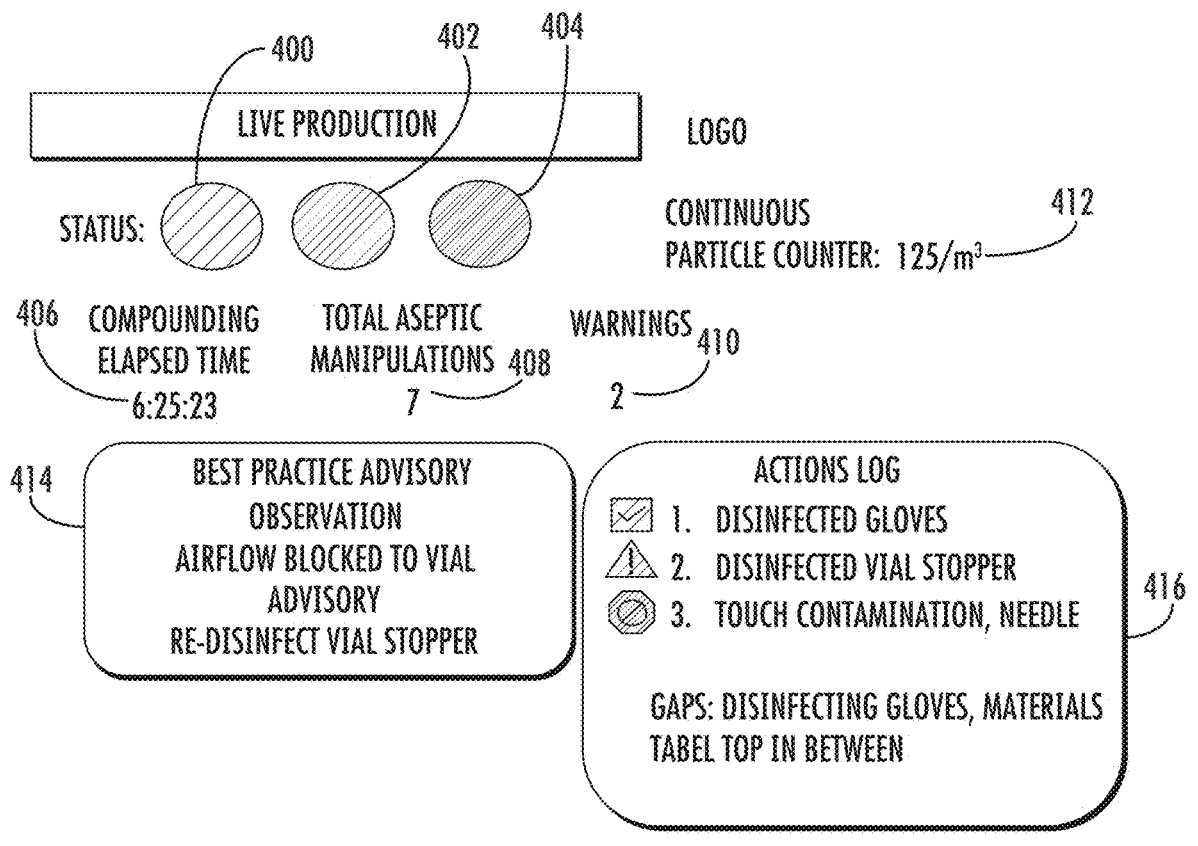
FIG. 4 is a diagram illustrating an exemplary dashboard interface that may be displayed by an automated aseptic technique evaluator.

Automated aseptic technique evaluator 310 may be trained to identify each of the above-referenced task phases for compounding in a horizontal airflow compounding hood, determine a probability that one or more of the errors referenced above have occurred, if the probability exceeds a threshold, determine that the error has occurred, and generate output indicative of the errors that have occurred (step 5 above). In one example, the output may be in a dashboard format, an example of which is illustrated in FIG. 4. In FIG. 4, the dashboard interface includes green, yellow, and red status indicators 400, 402, and 404, which respectively indicate whether the performance of a particular compounding task phase is good, needing improvement, or bad, for example, depending on the number and types of errors made. The dashboard interface further includes a compounding time display 406 indicating an elapsed time since a start of a compounding task. The dashboard interface further includes a counter 408 of total aseptic manipulations made during the compounding task. The dashboard interface further includes a warnings counter 410 that indicates the number of warnings generated for the compounding task. The dashboard interface further includes a continuous particle counter 412 which indicates a continuous particle count detected by a particle count sensor that may be integrated within the compounding hood. The interface further includes a best practices advisory area 414 which displays to the student/user in real time during compounding best practice advisory actions that can be implemented to improve the current aseptic compounding task. The dashboard interface further includes an action log 416 where actions performed and logged by automated aseptic technique evaluator 310 during the compounding task are displayed. A status indicator is displayed adjacent to each displayed action and indicates whether the action should have been performed, should not have been performed, or still needs to be performed. It should be noted that the interface shown in FIG. 4 is an example, and automated aseptic technique evaluator 310 may generate an interface with the same or different elements from those shown in FIG. 4 without departing from the scope of the subject matter described herein.

Table 1 shown below illustrates exemplary dashboard elements that automated aseptic technique evaluator 310 may display to the student/user via the dashboard interface.

TABLE 1

| Exemplary Dashboard Interface Elements | |
| --- | --- |
| Overall Category for Monitoring | Specific Activity that would be displayed on dashboard and report created |
| Bar code scanning for each individual product | Recognition that each individual product was bar code scanned Compliance reporting for overall scanning rate |
| Compounding time and error and error severity (e.g., low, medium, high) measures | Compounding time segmented for individual students/users Compounding time segmented for individual products Compounding time segmented for individual batches Each error categorized on potential for harm if reached a patient |
| Compliance reminders for different operational practices | Reminder to change gloves every 30 minutes Reminder to remove gown on a periodic basis Reminder to regularly disinfect the compounding hood Reminder to consider allowable/advisable contact time for different chemical cleaning agents Reminder to spray gloves following removal from the compounding hood Reminder for compounders moving between compounding hoods to consider possible differences between compounding hoods |
| Appropriate positioning/ Ergonomics | Notification of correct/incorrect hand and product positioning in the compounding hood Notification if hand removed then re-entered or vial/product removed then re-entered or head entered compounding hood Notification if greater than one product placed into compounding hood at a time; notification if vial not removed after product prepared Notification of incorrect positioning of items within the compounding hood (too close to front or side; blockage of airflow) |
| Reconstitution of an IV lyophilized powder | Each product has a time for dissolution, and this will be analyzed for appropriateness |

According to another aspect of the subject matter described herein, a smart compounding or research hood is provided. The smart compounding or research hood may comprise a housing forming an enclosure, such as that illustrated in FIG. 1 for pharmaceutical compounding or research. The smart compounding or research hood may include a fan for creating airflow in a desired direction in the hood. The smart compounding or research hood may include one or more sensors for recording data from which positions and/or orientation of objects within the enclosure can be determined. The sensors, in one example, may include video cameras for recording video of the objects within the enclosure. The smart compounding or research hood may include or be associated with software for determining the positions and/or orientations of the objects within the hood based on the data from the sensors and while the user is performing a compounding or research task. For example, the software may include the gloved hand tracker or other tracking model that is trained to track positions and orientations of objects within the enclosure. The output of the model can then be used to evaluate the compounding or research task being performed.

FIG. 5 is a flow chart illustrating an exemplary process for automated assessment of aseptic technique. Referring to FIG. 5, in step 500, the process includes collecting, using sensors positioned in or around a compounding hood, data from which positions, orientations, and movements of objects used in an aseptic compounding task can be determined. For example, cameras, other optical sensors, and/or IoT devices may be positioned in or around a compounding hood to record video or other data from which object identification, motion, and orientation can be determined.

In step 502, the process includes feeding the data from which the positions, orientations, and movements of the objects can be determined into an automated aseptic technique evaluator. For example, the sensors may feed the video data via a wireless or wired interface to automated aseptic technique evaluator 310 executing on a computing platform for classifying and evaluating the data. The video data may be raw video data and timing information associated with each video frame. From this data, object classifications, orientations, and movements can be determined.

Figure 6:
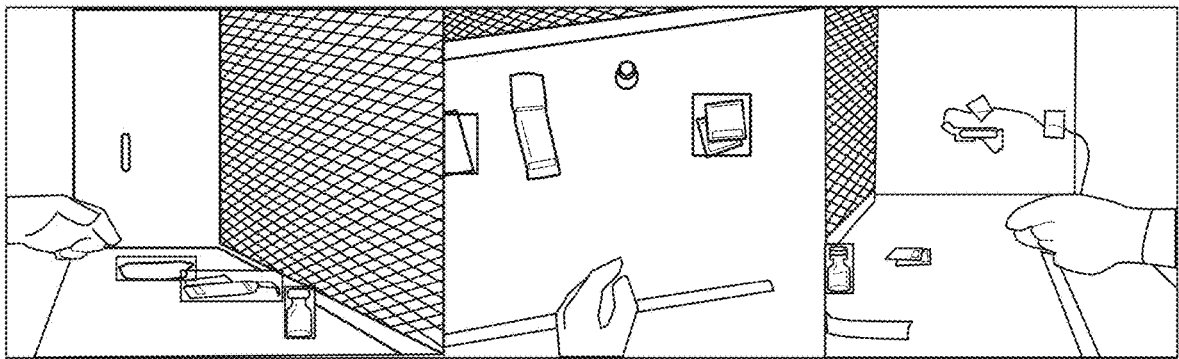
FIG. 6 illustrates images of classified objects in a compounding hood.

In step 504, the process includes identifying, using the automated aseptic technique evaluator and from the data, phases of the aseptic compounding task. For example, automated aseptic technique evaluator 310 may utilize the trained machine learning classifiers described above to identify objects and to recognize phases of an aseptic compounding task. FIG. 6 illustrates images of objects in a compounding hood that are classified using a machine learning classifier. In the illustrated example, the objects surrounded by green boxes have been classified and include a syringe, a vial, and alcohol wipes. The student's/user's hands and portions of the compounding hood are also shown.

In step 506, the process includes automatically detecting, by the automated aseptic technique evaluator, errors occurring during at least some of the phases. For example, automated aseptic technique evaluator 310 may implement the classifiers described above to determine whether or not errors occur during each phase of the task.

In step 508, the process includes generating and displaying, by the automated aseptic technique evaluator, output indicative of the errors. For example, automated aseptic technique evaluator 310 may generate and display output, such as the dashboard interface illustrated in FIG. 5, that indicates the errors detected during the aseptic compounding task.

Gloved Hand Tracking Algorithm

As described above, one aspect of the subject matter described herein includes tracking position, orientation, and movement of the gloved hands of a user performing an aseptic compounding task. Tracking gloved hands presents a different problem than tracking ungloved hands, because the gloves hide some of the features of the hand, which makes tracking position, orientation, and movement more challenging. Performing gloved hand tracking involves several steps to generate a trained model to accurately track the position, orientation, and movement of a compounder's hands. One step is data collection and annotation. To train the model, a large dataset of hand movements is collected, ideally by sensing of multiple compounders wearing different color gloves from multiple perspectives performing different techniques. The data may be video frames or data from other types of sensors capable of capturing data from which positions and orientations of objects can be determined. This dataset is separated into individual frames and then a large selection of frames is annotated with precise information about the position and orientation of the hands in 3D space, using software to allow for identifying key positions on the fingers, wrists, and forearms. The annotation consists of key point, bounding box, and occlusion annotations performed using Amazon Web Services' Ground Truth annotation tool, which is an online portal that allows for manual annotation of images.

Figures 7A, 7B, 7C:
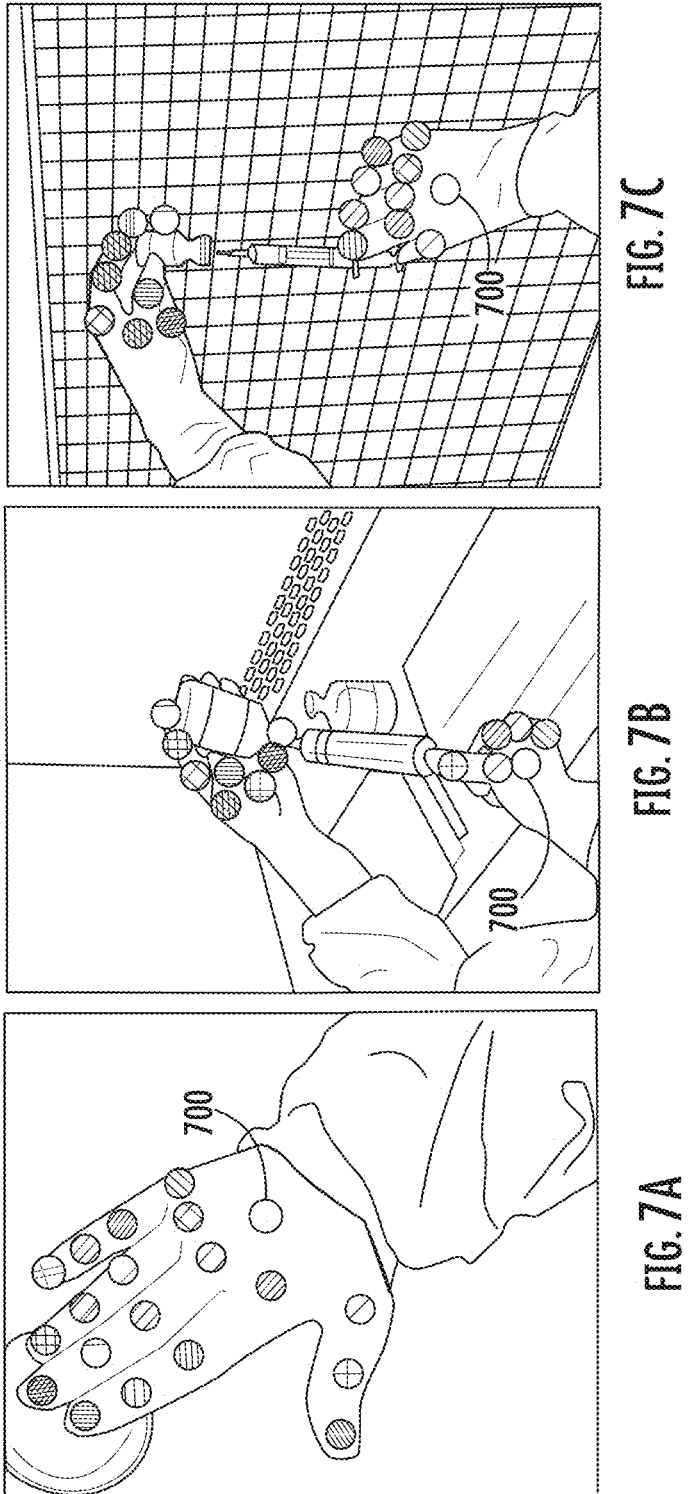
FIGS. 7A-7C illustrate the identification of features of gloved hands of a user in performing a compounding task.

FIG. 7A-7C illustrate results of annotation of three different frames showing gloved hands of a user performing a compounding task. In FIGS. 7A-7C, the circles overlaid on the images represent features of the user's hands whose position, orientation, and movement will be tracked. For example, circle 700 represents the same tracked position on the back of the user's hands in the different frames. The other circles represent similar features, such as knuckles, finger tips, joints, etc.

One task in selecting data for training the hand tracking model is to select frames or frame sequences showing varying positions and orientations and to include occlusion by or around objects in the environment. The next step is machine learning model development. Machine learning techniques, such as deep learning, are employed to create the hand tracking model. The hand tracking model is trained using Nvidia's TAO toolkit, which provides a model zoo of pre-trained models for various applications (object detection, bounding boxes, key point estimation, etc.) The hand tracking model utilizes a Fiducial Points Estimator as its base. In one example, the base model is fpenet_trainable_v1.0 available from Nvidia NGC. The model is then trained on task-specific video data, i.e., video of users performing compounding tasks within a compounding hood, using transfer learning.

The hand tracking model tracks the position, orientation, and movements of the gloved hands of the user by identifying the features illustrated in FIGS. 7A-7C and tracking those features across frames. The dataset described in the preceding paragraph is used to train the model, which learns to recognize patterns in hand movements and associations between sensor data and corresponding hand poses and orientations. The next step is model optimization. The trained model may require iteration and fine-tuning of parameters to achieve better performance, reducing tracking errors and improving real-time responsiveness.

The trained model can be incorporated into automated aseptic technique evaluator 310, which uses the model to track positions, orientations, and movements of the user's gloved hands as the user performs compounding tasks. Automated aseptic technique evaluator 310 may use the tracked movements of the user's hands to identify phases of the aseptic compounding task. For example, the tracked positions of the user's thumb and index finger in FIGS. 7B and 7C may be used to identify withdrawal of a compound from a vial using a syringe.

The disclosure of each of the following references is incorporated herein by reference in its entirety.

REFERENCES

1. New England Compounding Center meningitis outbreak: https://en.wikipedia.org/wiki/New_England_Compounding_Center_meningitis_outbreak (last accessed Mar. 1, 2019).

2. Statement of Janet Woodcock, M.D. before the subcommittee on health of the committee on energy and commerce—'Reforming the drug compounding regulatory framework; Jul. 16, 2013: http://docs.house.gov/meetings/IF/IF14/20130716/101137/HHRG-113-IF14-Wstate-WoodcockJ-20130716-U1.pdf (last accessed Mar. 1, 2019).

3. Shehab N, Brown M N, Kallen A J, and Perz J F. U S Compounding Pharmacy-Related Outbreaks, 2001-2013: Public Health and Patient Safety Lessons Learned. Journal of Patient Safety 2018; 14(3): 164-173.

4. Woodcock J and Dohm J. Toward Better-Quality Compounded Drugs—an Update from the FDA. New England Journal of Medicine 2017; 377(26): 2509-2512.

5. Vonberg R P and Gastmeier P. Hospital-acquired infections related to contaminated substances. Journal of Hospital Infection 2007; 65:15-23.

6. Morris A M, Schneider P J, Pedersen C A, and Mirtallo J M. National survey of quality assurance activities for pharmacy-compounded sterile preparations. American Journal of Health-System Pharmacy 2003; 60:2567-2576.

7. Newton D W. United States Pharmacopeia Chapter <797> Timeline: 1989 to 2013. International Journal of Pharmaceutical Compounding 2013; 17(4): 283-288.

8. Myers C E. History of sterile compounding in US hospital: Learning from the tragic lessons of the past. American Journal of Health-System Pharmacy 2013; 70:1414-1427.

9. Newton D W and Trissel L A. A primer on USP Chapter <797>: "Pharmaceutical compounding sterile preparations," and USP Process for Drug and Practice Standards. International Journal of Pharmaceutical Compounding 2004; 8(4): 251-263.

10. Triad Rx, Inc U S Food & Drug Administration Form 483 Warning letter: Feb. 5, 2019: https://www.fda.gov/ICECI/EnforcementActions/WarningLetters/ucm631101.htm (last accessed Mar. 1, 2019).

11. Lee R K and Shrewsbury R P. Comparison of observational evaluations and potency analyses to assess aseptic techniques of student compounders. Accepted for publication: American Journal of Pharmaceutical Education.

12. Kastango E S. A practical guide to aseptic technique verification: policies and procedures that meet USP Chapter <797> requirements. Pharmacy Purchasing Products 2005 (April); 16-18 https://www.pppmag.com/documents/V2N2/Aseptic.pdf (last accessed Mar. 1, 2019).

13. Moody C A, Eckel S F, and Amerine L B. Evaluating the sensitivity of a media-fill challenge test under various situations as a reliable method for recommended aseptic technique competency assessment. Journal of Pharmacy Technology 2016; 32(2): 47-53.

14. Accreditation Council for Pharmacy Education: PharmD Program Accreditation. ACPE Standard 2016 https://www.acpe-accredit.org/pdf/Standards2016FINAL.pdf (last accessed Mar. 1, 2019).

15. Instruction on compounded sterile preparations at schools of pharmacy. American Journal of Health-System Pharmacy 2018; 75(12): 847-849.

It will be understood that various details of the subject matter described herein may be changed without departing from the scope of the subject matter described herein. Furthermore, the foregoing description is for the purpose of illustration only, and not for the purpose of limitation, as the subject matter described herein is defined by the claims as set forth hereinafter.

What is claimed is:

1. A method for automated assessment of aseptic technique of compounding in a compounding hood, the method comprising:

collecting, using sensors positioned in or around a compounding hood, data from which positions, orientations, and movements of objects used in an aseptic compounding task can be determined;

feeding the data into an automated aseptic technique evaluator;

identifying, using the automated aseptic technique evaluator and from the data, phases of the aseptic compounding task;

automatically detecting, by the automated aseptic technique evaluator, errors occurring during at least some of the phases, wherein automatically detecting the errors includes mapping the positions of objects into a three-dimensional coordinate system, determining, from the positions of the objects, a path taken by the object in the three-dimensional coordinate system, quantitatively defining a three-dimensional region in the three-dimensional coordinate system indicating a path tolerance for aseptic technique in the three-dimensional coordinate system, and determining non-compliance with aseptic technique when the path taken is outside of the quantitatively defined three-dimensional region; and generating and displaying, by the automated aseptic technique evaluator, output indicative of the errors.

2. The method of claim 1 wherein collecting the data using the sensors positioned in or around the compounding hood includes collecting the data using cameras or other optical or other types of sensors positioned in or around the compounding hood.

3. The method of claim 1 wherein collecting the data using the sensors positioned in or around the compounding hood includes collecting the data using Internet of Things (IoT) sensors located on compounding instruments or compounding materials.

4. The method of claim 1 wherein identifying the phases includes applying a computer-vision-based or equivalent sensor-based object detection model to identify the objects.

5. The method of claim 1 wherein identifying the phases includes using a computer-vision-based or equivalent sensor-based pose estimation model to create time series data representing positions and orientations of the objects at different times.

6. The method of claim 5 wherein identifying the phases includes utilizing task phase identification heuristics to identifying each phase.

7. The method of claim 1 wherein identifying the phases includes identifying features of a user's gloved hands from the data collected from the sensors and tracking position, orientation, and movement of the identified features in different frames of the data.

8. The method of claim 1 wherein automatically detecting the errors includes applying a classification model that generates, for each phase, a probability score indicative of a likelihood of occurrence of an error and determining that the error has occurred when the score exceeds a threshold value.

9. The method of claim 1 wherein generating and displaying the output includes generating and displaying a dashboard interface that indicates the errors that occurred during performance of the aseptic compounding task.

10. The method of claim 9 wherein the dashboard interface displays in real time during performance of the aseptic compounding task best practice advisory actions for a student/user to perform during the aseptic compounding task, or in batch after performance of aseptic compounding tasks assessment of performance during the aseptic compounding tasks.

11. The method of claim 1 wherein the automated aseptic technique evaluator is implemented using at least one trained machine learning classifier.

12. A system for automated assessment of aseptic technique of compounding in a compounding hood, the system comprising:

at least one processor;

a plurality of sensors positionable in or around a compounding hood for collecting data from which positions, orientations, and movements of objects used in an aseptic compounding task can be determined; and an automated aseptic technique evaluator implemented using the at least one processor for receiving the data, identifying from the data phases of the aseptic compounding task, automatically detecting errors occurring during at least some of the phases, and generating and displaying output indicative of the errors, wherein automatically detecting the errors includes mapping the positions of objects into a three-dimensional coordinate system, determining, from the positions of the objects, a path taken by the object in the three-dimensional coordinate system, quantitatively defining a three-dimensional region in the three-dimensional coordinate system indicating a path tolerance for aseptic technique in the three-dimensional coordinate system, and determining non-compliance with aseptic technique when the path taken is outside of the quantitatively defined three-dimensional region.

13. The system of claim 12 wherein the sensors comprise cameras or other optical or other types of sensors positionable in or around the compounding hood.

14. The system of claim 12 wherein the sensors comprise Internet of Things (IoT) sensors locatable on compounding instruments or compounding materials.

15. The system of claim 12 wherein the automated aseptic technique evaluator is configured to use a computer-vision-based or equivalent sensor-based object detection model to identify the objects.

16. The system of claim 15 wherein the automated aseptic technique evaluator is configured to use a computer-vision-based or equivalent sensor-based pose estimation model to create time series data representing positions and orientations of the objects at different times.

17. The system of claim 16 wherein the automated aseptic technique evaluator is configured to utilize task phase identification heuristics to identify each phase.

18. The system of claim 12 wherein the automated aseptic technique evaluator is configured to identify the phases by identifying features of a user's gloved hands from the data collected from the sensors and tracking position, orientation, and movement of the identified features in different frames of the data.

19. The system of claim 12 wherein the automated aseptic technique evaluator is configured to detect the errors by applying a classification model that generates, for each phase, a probability score indicative of a likelihood of occurrence of an error and determining that the error has occurred when the score exceeds a threshold value.

20. The system of claim 12 wherein the automated aseptic technique evaluator is configured to generate a dashboard interface that indicates the errors that occurred during the performance of the aseptic compounding task.

21. The system of claim 12 wherein the automated aseptic technique evaluator is implemented using at least one trained machine learning classifier.

22. A non-transitory computer readable medium having stored thereon executable instructions that when executed by the processor of a computer control the computer to perform steps comprising:

collecting, using sensors positioned in or around a compounding hood, data from which positions, orientations, and movements of objects used in an aseptic compounding task can be determined;

feeding the data into an automated aseptic technique evaluator;

identifying, using the automated aseptic technique evaluator and from the data, phases of the aseptic compounding task;

automatically detecting, by the automated aseptic technique evaluator, errors occurring during at least some of the phases, wherein automatically detecting the errors includes mapping the positions of objects into a three-dimensional coordinate system, determining, from the positions of the objects, a path taken by the object in the three-dimensional coordinate system, quantitatively defining a three-dimensional region in the three-dimensional coordinate system indicating a path tolerance for aseptic technique in the three-dimensional coordinate system, and determining non-compliance with aseptic technique when the path taken is outside of the quantitatively defined three-dimensional region; and generating and displaying, by the automated aseptic technique evaluator, output indicative of the errors.

\* \* \* \* \*